United States Patent [19]

Stevens

[11] Patent Number: 4,762,617

[45] Date of Patent: Aug. 9, 1988

[54] SIZE-EXCLUSION CHROMATOGRAPHY SYSTEM FOR MACROMOLECULAR INTERACTION ANALYSIS

[75] Inventor: Fred J. Stevens, Downers Grove, Ill.

[73] Assignee: The United States of America as represented by the United States Department of Energy, Washington, D.C.

[21] Appl. No.: 3,667

[22] Filed: Jan. 15, 1987

[51] Int. Cl.$^4$ .............................................. B01D 15/08
[52] U.S. Cl. ................................ 210/635; 210/198.2; 210/656; 73/61.1 C; 422/70; 436/161; 530/417
[58] Field of Search ............ 210/656, 659, 635, 198.2; 422/70; 73/61.1 C; 530/413, 417; 436/161, 162

[56] References Cited

U.S. PATENT DOCUMENTS

| | | | |
|---|---|---|---|
| 3,706,381 | 12/1972 | Joynes | 422/70 |
| 3,918,913 | 11/1975 | Stevenson et al. | 273/425.6 |
| 3,985,021 | 10/1976 | Achener et al. | 210/61.1 G |
| 4,003,243 | 1/1977 | Blu | 210/198.2 |
| 4,073,725 | 2/1978 | Takeuchi et al. | 210/198.2 |
| 4,158,630 | 6/1979 | Stearns | 210/198.2 |
| 4,181,853 | 1/1980 | Abu | 436/161 |
| 4,186,607 | 2/1980 | Porter et al. | 73/422 GC |
| 4,364,263 | 12/1982 | Sankoorikal et al. | 73/61.1 C |
| 4,429,584 | 2/1984 | Beyer et al. | 73/864.21 |
| 4,468,331 | 8/1984 | Antle et al. | 210/659 |
| 4,472,354 | 9/1984 | Passell et al. | 422/62 |
| 4,478,713 | 10/1984 | Girot | 210/198.2 |
| 4,498,774 | 2/1985 | Yeung | 422/70 |
| 4,532,043 | 7/1985 | Prudhomme | 210/635 |
| 4,578,990 | 4/1986 | Abbott et al. | 73/55 |
| 4,595,495 | 6/1986 | Yotum | 210/198.2 |
| 4,595,496 | 6/1986 | Carson | 210/198.2 |

FOREIGN PATENT DOCUMENTS

| | | | |
|---|---|---|---|
| 57-63449 | 4/1982 | Japan | 210/198.2 |
| 2128167 | 4/1984 | United Kingdom | 210/198.2 |
| 602968 | 3/1978 | U.S.S.R. | 210/198.2 |

OTHER PUBLICATIONS

FASEB Abstract, "Antibody-Antigen Interaction: Application of Chromatography Simulation and Laboratory Microcomputer" Stevens and Ainsworth (1985).
Stevens and Ainsworth, Biophysical Society Meeting, Feb. 9, 1986, Abstract and Poster, "Microcomputer Controlled Size-Exclusion Chromatography: Application to Analysis of Macromolecular Interactions.
Stevens et al, LC.GC., vol 4, No. 4, "Macromolecular Interactions: Application of Microcomputer-Controlled, High Speed Size-Exclusion Chromatography, 1986.
Stevens, Biochemistry. 1986, 25, 981, "Analysis of Protein-Protein Interaction by Simulation of Small Zone Size-Exclusion Chromatography: Application to an Antibody-Antigen Association.
Kohler et al., "Comparative Liquid Chromatography by Automatic Repetitive Injection," American Laboratory, vol. 11, No. 1 (Jan. 1979) pp. 75–79.
Mills et al., "An Automatic System for Chromatographic Analysis".
Literature by Dynatech Precision Sampling Corporation, Box 15886, Baton Rough, La. 70895, on "The Model LC 241 Automatic Sample Injector".
Document from the Biochemical Society, London, England, 1981, by Fred J. Stevens and Marianne Schiffer of Argonne National Laboratory, Argonne, Ill., entitled "Computer Simulation of Protein Self-Association During Small-Zone Gel Filtration."

Primary Examiner—Ernest G. Therkorn
Attorney, Agent, or Firm—Hugh W. Glenn; Robert J. Fisher; Judson R. Hightower

[57] ABSTRACT

A low pressure, microcomputer controlled system employing high performance liquid chromatography (HPLC) allows for precise analysis of the interaction of two reversibly associating macromolecules such as proteins. Since a macromolecular complex migrates faster than its components during size-exclusion chromatography, the difference between the elution profile of a mixture of two macromolecules and the summation of the elution profiles of the two components provides a quantifiable indication of the degree of molecular interaction. This delta profile is used to qualitatively reveal the presence or absence of significant interaction or to rank the relative degree of interaction in comparing samples and, in combination with a computer simulation, is further used to quantify the magnitude of the interaction in an arrangement wherein a microcomputer is coupled to analytical instrumentation in a novel manner.

16 Claims, 4 Drawing Sheets

SIZE-EXCLUSION CHROMATOGRAPHY SYSTEM FOR MACROMOLECULAR INTERACTION ANALYSIS

CONTRACTUAL ORIGIN OF THE INVENTION

The United States Government has rights in this invention under Contract No. W-31-109-ENG-38 between the U.S. Department of Energy and Argonne National Laboratory.

BACKGROUND OF THE INVENTION

This invention relates generally to analytical instrumentation for determining macromolecular interaction and is particularly directed to a microcomputer controlled chromatography system employing size exclusion and gel filtration for the qualitative and quantitative analysis of the interaction of macromolecules such as proteins.

The interaction of macromolecules results in the formation of a noncovalently assembled complex that is characterized by a larger Stokes radius than that of either of its constituents. Therefore, ultracentrifugation, inelastic light scattering, and size-exclusion chromatography (SEC), each of which depends upon the Stokes radius of a macromolecule, have been applied in protein-protein association studies. The general availability, conceptual directness, and minimal expense of SEC suggests that this procedure should be a practical approach to many problems of macromolecular interaction analysis if quantitative reproducibility can be ensured. Size-exclusion gel filtration has thus been used to qualitatively study the interaction between two proteins on the basis of a dependence of observed elution positions on sample concentration, wherein the filtration time is dependent on the size of the particles. The formation of a stable, higher molecular weight species by a mixture of two proteins has been observed in the case of high affinity interaction. The Hummel-Dreyer technique has frequently been used for quantitative chromatographic evaluation of interaction by analysis of a small zone of ligand on a column saturated with the binding molecule. Thus, a column saturated with a DNA plasmid has been used to measure the affinity of a restriction enzyme for its nucleic acid binding site. Large zone SEC analyses based on interpretation of the shape of the boundary profile or the median position of the sample plateau of the mixture have been extensively studied.

To conserve potentially rare or irreplaceable biological molecules, however, a small zone gel-chromatography strategy is desirable. Quantitative interpretation of small-zone elution profiles has been hindered by the absence of a definitive mathematical description of the dynamic behavior of a sample of interacting solutes during development of the chromatogram. Approximate solutions have been developed which appear to be appropriate for experimental strategies in which one solute is in sufficient excess to generate pseudo first-order reaction kinetics and have allowed for analysis of interactions observed by size-exclusion high performance liquid chromatography (HPLC). In another approach, an iterative computer simulation of the elution process has shown promise for both qualitative and quantitative interpretation of small zone chromatograms. See F. J. Stevens and M. Schiffer, Biochem. J. 195, 213-219 (1981).

Although HPLC provides an appropriate analytical system for studying the degree of interaction between macromolecules in terms of precision, reproducibility and speed, contemporary silica-based HPLC size-exclusion matrices retain interactions with proteins that preclude the use of HPLC columns for quantitative studies. To overcome this problem as well as other problems encountered in the prior art, the present invention contemplates a hybrid system, combining microcomputer control of sample injection and data collection, an HPLC pump, and a commercially available cross-linked agarose resin packed in columns as small as 1 mL volume. The present invention is capable of demonstrating interactions of proteins and nucleic acids, antisera and antigen, monoclonal anti-idiotypic antibody and idiotype, as well as autoimmune rheumatoid factor and IgG. The principles of the present invention may be used commercially as a research tool, for quality control of tests involving monoclonal antibodies, and for various other purposes.

OBJECTS AND SUMMARY OF THE INVENTION

Accordingly, it is an object of the present invention to provide precise analysis of the interaction of macromolecules.

Another object of the present invention is to provide a microcomputer controlled, size exclusion-based system and method employing gel filtration for analyzing macromolecular interaction.

A further object of the present invention is to provide an improved combination for analyzing macromolecular interactions which requires smaller samples and conserves potentially rare or irreplaceable biological molecules.

A still further object of the present invention is to provide a fast (approximately 30 minutes) method for accurately analyzing the interaction of minute quantities (as small as 50 ng) of macromolecular substances.

Still another object of the present invention is to provide an iterative computer simulation of the elution process between interacting macromolecular solutes which is useful in both the qualitative and quantitative interpretation of small zone chromatograms.

It is yet another object of the present invention to provide an improved arrangement for rapidly comparing interacting macromolecular reagents or for quality control of applications of monoclonal antibodies directed against protein antigens.

Yet another object of the present invention is to provide a quantitative, small zone, computer controlled chromatographic system for providing actual and calculated data on experimental and theoretical protein-protein interactions.

The present invention combines the precision and sensitivity of HPLC methods with the use of a commercially obtained cross-linked agarose resin to minimize protein interaction with the matrix in a microcomputer controlled hybrid gel permeation chromatography system which provides profiles of actual and various expected degrees of interaction between macromolecules, such as a protein-protein system, under investigation. The microcomputer controlled system is capable of analyzing as little as 50 ng of protein in approximately 30 minutes and provides quantitative measurements useful in an understanding of the protein-protein interaction. A comparison of elution profile of a mixture of two proteins with an elution profile synthesized by summation of the profiles exhibited by the two proteins individually effectively generates an interaction index related to the association constant ($K_a$) governing the interaction between the two proteins A and B such that $c = k_a ab$, where c, a and b are the (molar) equilibrium concentrations of the complex and the two constituents, respectively. An interaction index may in some cases provide a suitable alternative to an evaluation of the thermodynamic $k_a$. The interaction index is also useful as a rapid means of comparing interacting macromolecular reagents or as a quality control technique for developing applications of monoclonal antibodies directed against protein antigens.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

DESCRIPTION OF PREFERRED EMBODIMENT

Figure 1:
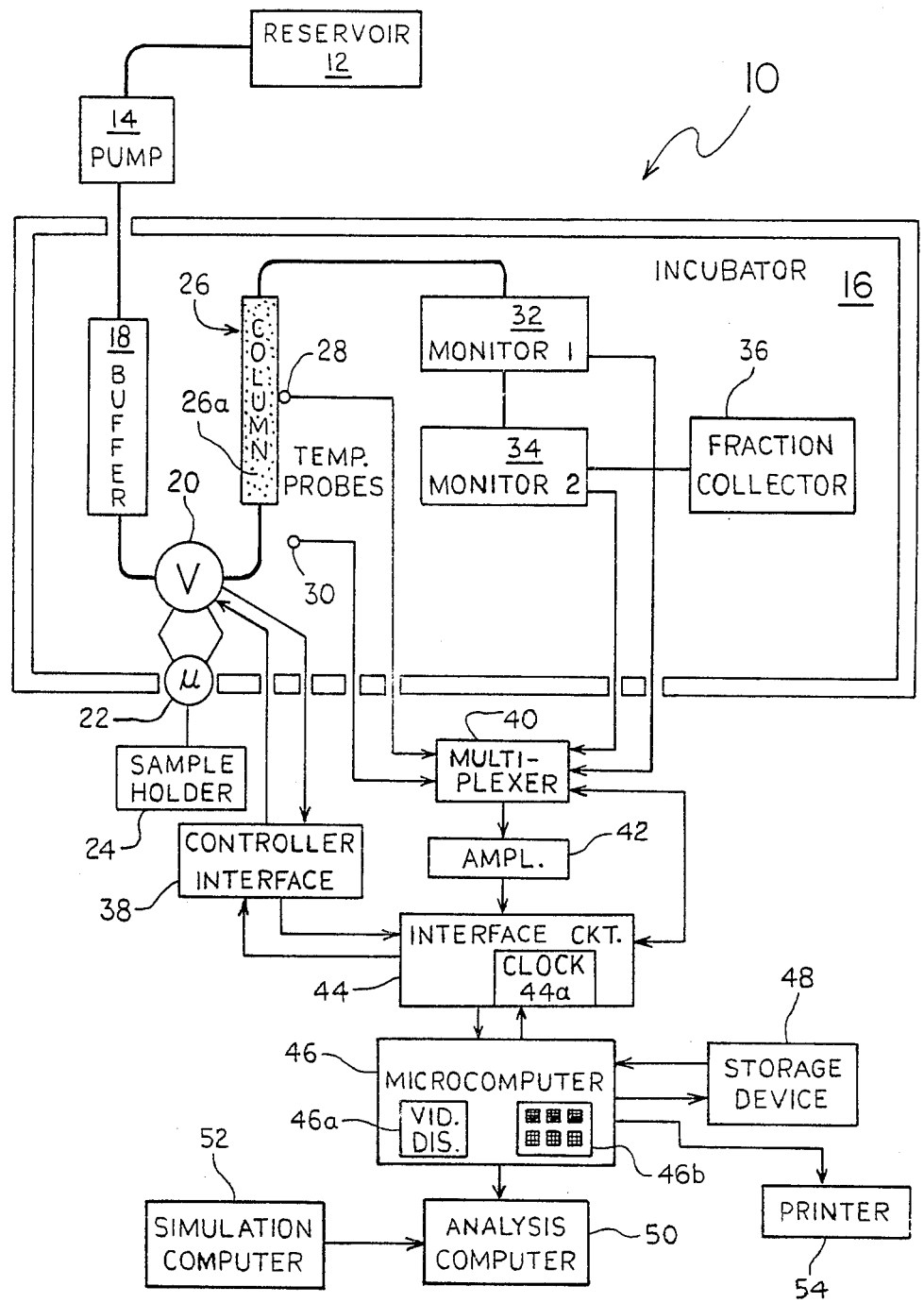
FIG. 1 is a simplified block diagram of a size-exclusion chromatography system for macromolecular interaction analysis in accordance with the present invention.

Referring to FIG. 1, there is shown a simplified schematic and block diagram of a HPLC-based, size exclusion chromatography system 10 for analyzing macromolecular interactions in accordance with the present invention.

The chromatography system 10 includes a reservoir 12 containing a solvent which is provided to a buffer 18 within an incubator 16 by means of a pump 14. In a preferred embodiment, solvent flow is maintained by a Model 2150 HPLC pump available from LKB Instruments of Gaithersburg, MD., equipped with titanium heads to accommodate long term use of aqueous saline buffers where the buffer is provided with the solvent in the reservoir 12. The buffer saline solution may also be provided via a buffer supply 18 coupled to the pump 14. The samples to be analyzed are contained in a sample holder 24 and are provided to a multiposition valve 20 via a microvalve 22. The valve used in a preferred embodiment is an MV-7 motorized, multiposition valve available from Pharmacia Company of Piscataway, N.J. The various postions of the multiposition valve 20, i.e., load, inject and wash, are controlled by a microcomputer 46 through an interface circuit 44 and a controller interface circuit 38 which allow the microcomputer to communicate with the multiposition valve 20 through an ADALAB interface circuit board obtained from Interactive Microwave Company of state College, Pa. The controller interface circuit 38 decodes microcomputer commands to the multiposition valve 20 and translates valve signals to the microcomputer 46. The solvent and sample flow from the multiposition valve 20 is provided to an HPLC column 26 which contains a cross-linked agarose resin to minimize interaction between the solvent and the matrix. The microvalve 20 is manually operated and permits small amounts of precisely measured sample to be provided to the HPLC column 26 under the control of the microcomputer 46. The effluent from the column 26 is preferably monitored at 280 nm in an HRJ-10 10-mm flow cell 32 (also available from Pharmacia Company) with an illuminated volume of 8.7 $\mu L$. The monitor signal is passed through a software selectable multiplexer 40 and is amplified by an amplifier 42 containing an ADALAB interface board before conversion by an analog-to-digital (A/D) converter in the interface circuit 44 which also includes a clock circuit 44a. Various column configurations may be used in accordance with the present invention as described in the following paragraphs. Mobile phases are 0.15 M NaCl, phosphate buffered to a pH of 7.2, in a preferred embodiment. The temperature of the column 26 is monitored by first and second temperature probes 28, 30, with appropriate outputs provided to the multiplexer 40.

The chromatography system 10 may also include a second flow cell monitor 34 coupled to the first flow cell monitor 32 for receiving samples for analysis. The second flow cell monitor 34 is preferably coupled to a fraction collection 36 also located within the incubator 16 for recovery of the samples under analysis. The control microcomputer 46 is also coupled to a data storage device 48, which in a preferred embodiment is a two disk drive system. Data collection is conducted by a program written in Applesoft BASIC and supplemented by the Quick Input/Output (I/O) ADALAB operating language. In a preferred embodiment, the control microcomputer 46 is an Apple IIe microcomputer. The control microcomputer 46 performs two principal roles in data collection: (1) control of sample injection and (2) calculation and storage of the digitalized monitor voltage during a sample analysis run. More specifically, the control microcomputer 46, which in a preferred embodiment includes a video display 46a and a user input responsive keyboard 46b, documents each sample run, collects data, writes data into and reads data from the storage device 48, and sends the thus recalled data to the analysis computer 50 via a telephone data link.

For further analyses, selected data sets are transferred from the storage device 48 via the control microcomputer 46 to an analysis computer 50, which in a preferred embodiment is a PDP11/44 minicomputer available from Digital Equipment Corp. The analysis computer 50 adds or subtracts measured chromatogram values in scaling the data. A telephone data transfer link between the microcomputer 46 and the analysis computer 50 is provided through a Kermit terminal emulator and file-transfer system such as available from Columbia University Center for Computing Activities, New York, N.Y. The digitized monitor voltages are converted to absorbance values and the baseline of the chromatogram is zeroed by a short program written in BASIC. Routine manipulations and comparisons of elution profiles are accomplished by use of Minitab software available from the Pennsylvania State University, University Park, Pa. A printer 54 coupled to the control microcomputer 46 may be used for obtaining a graphic illustration of the measured data.

Figure 2:
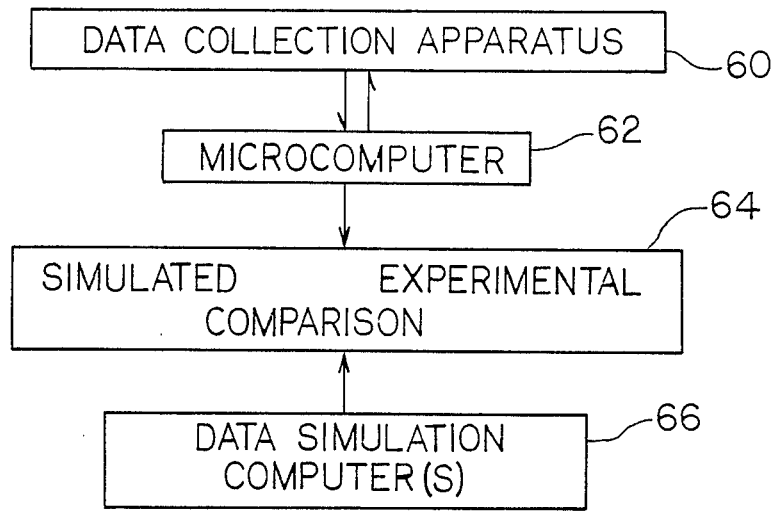
FIG. 2 is a functional block diagram of the size-exclusion chromatography system of FIG. 1.

Referring to FIG. 2, there is shown a functional block diagram of the size-exclusion chromatography system 5 shown in schematic block diagram form in FIG. 1. Experimental data are obtained in block 60 from suitable high performance liquid chromatography apparatus including the reservoir 12, the pump 14 and those components of the chromatography system 10 located within the incubator 16. Experimental reproducibility essential for quantitative comparison of chromatograms is facilitated by use of the control microcomputer illustrated as block 62 in the figure for experimental control and for storage of data in digitized form such as in the storage device 48. Experimentally obtained data are transferred from the storage device 48 via the microcomputer 46 to the analysis computer 50 by means of which comparisons are made to a systematically generated series of simulated chromatograms in block 64. The chromatograph simulations generated in block 66 may be performed either by means of the analysis computer 50 or, as in a preferred embodiment, by a simulation computer 52 coupled to the analysis computer. The simulations generated by the simulation computer 52 are first used to emulate the chromatographic behavior of the individual constituents of the interaction when chromatographed separately. The parameters controlling flow rate (velocity) and band spread (dispersion and diffusion) are varied by the control microcomputer 46 to optimize correlation of the simulated and experimental chromatograms. The simulated chromatograms of the mixture are then obtained by varying the association constant (and stoichiometry of interaction) in the simulation to optimize correlation. The association constant $K_a$ determined is tested by repeating the process for different concentrations and ratios of interacting molecules.

Figure 3:
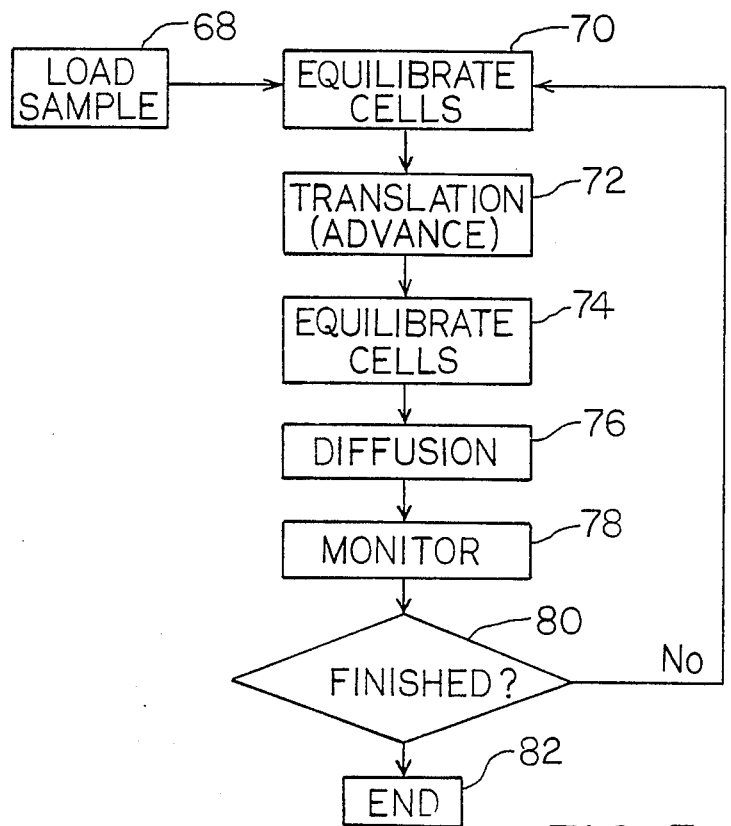
FIG. 3 is a simplified flow chart illustrating the interaction chromatography simulation utilized in the present invention.

Referring to FIG. 3, there is shown a simplified flow chart illustrating the interaction chromatography simulation utilized in the present invention in terms of the operations carried out under the control of the microcomputer 46 by the size-exclusion chromatography system 10 of the present invention. The algorithm used to emulate the interactive chromatography process consists of a model in which the size exclusion column is divided into an arbitrary number of independent cells, or a sequential array of compartments. At step 68, the sample is "loaded" and the process is initiated by assigning the "sample" of defined composition and concentration to the initial cells of the column 26 corresponding to the volume of the experimental sample. At step 70, the equilibrium distribution of free, mono-complexed and bi-complexed particles is calculated by implicitly assuming that the equilibration process is very rapid relative to the migration rate of the macromolecule such as a protein. At step 72, on the basis of free and complexed constituent velocities, and assuming complete interchange of molecules, average velocities of the interacting molecules, or components, during the simulation cycle are calculated. The average velocity for each component is determined for each cell based on the velocities of the components and the complex, or complexes if the ligand valence is two. Each component of velocity V is then advanced from cell I to cell I+V such that a Gaussian distribution about position I+V with standard deviation DISP is obtained. The Gaussian variance contributes dispersion to the simulated chromatogram. Each cell content is then re-equilibrated at step 74 as previously performed at step 70. A diffusion cycle is then undertaken at step 76 based on the gradient of the concentration of each component. The content of each cell is thus displaced to adjoining cells on the basis of the concentration gradient. The elution of the column 26 is monitored at step 78 by recording the concentration at a point past the column's terminus. The protein contents at the terminus of the post-column "monitor queue" are thus recorded and correspond to the chromatographic elution profile obtained during an experiment. At step 80, the program stored in the microcomputer 46 compares the number of iterations executed to a pre-set number of cycles (run length) and either terminates execution of the program by proceeding to step 82 or returns to step 70 and re-equilibrates the column. The entire process is then reiterated until a number of repetitions corresponding to the run length has been executed.

The simulation is applied by first generating runs to match the chromatographic characteristics of the interacting components run individually. The values for velocity, diffusion, and dispersion thus obtained are applied in simulated runs of a mixture of the two components. The association coefficient $K_a$ is varied systematically to obtain the maximum correlation with experimental data. The suitability of this value is tested by comparison of simulated and experimental elution profiles obtained at different initial concentrations of the interacting components.

Figure 4:
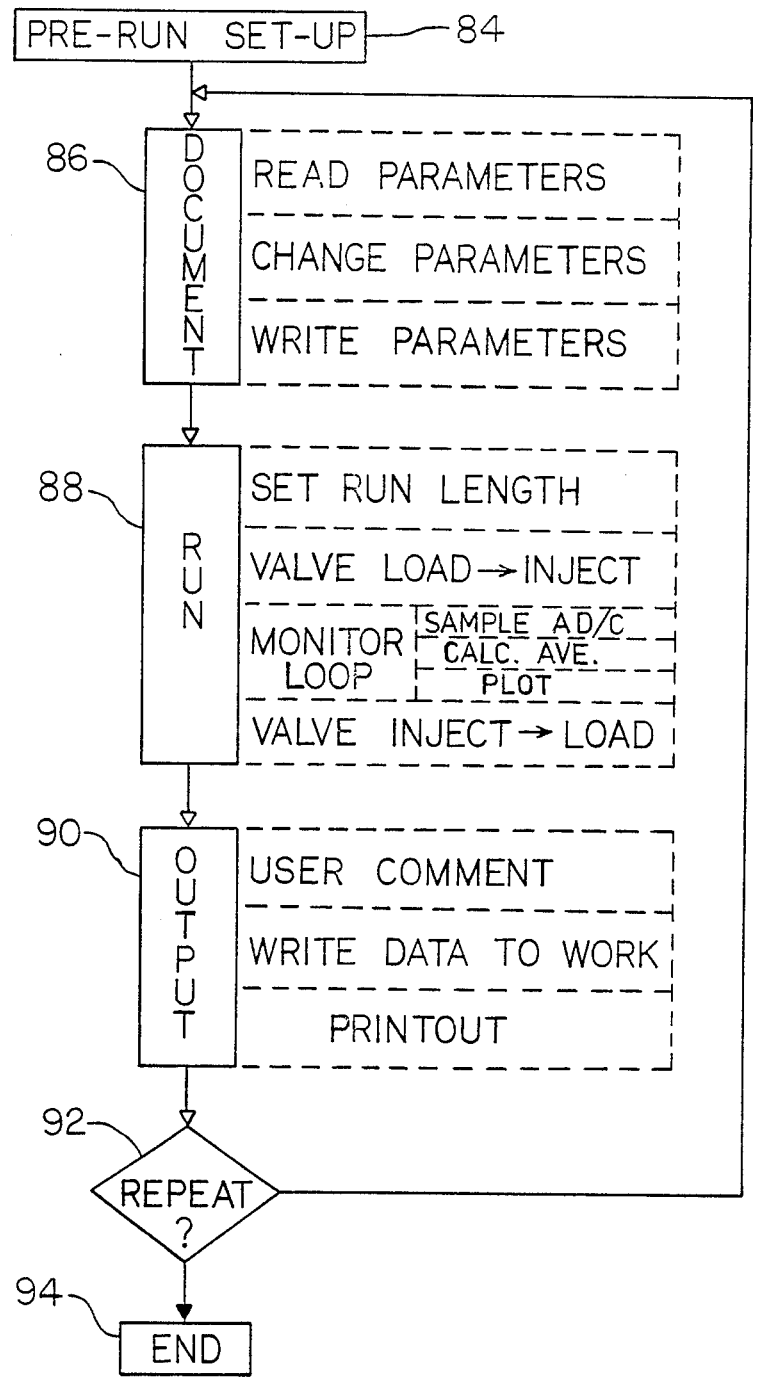
FIG. 4 is a simplified schematic representation of the organization of the data collection program stored in the microcomputer used to control the size-exclusion chromatography system of FIG. 1.

Referring to FIG. 4, there is shown a simplified schematic representation in the form of a flow chart of the data collection program stored in the control microcomputer 46 used to control the size-exclusion chromatography system 10 of the present invention. The program is initiated at step 84 when the date and time are entered by an operator. The time input sets the clock 44a in the interface circuit 44 in establishing a program start time. The program uses the start time of each run in combination with the calendar date to generate automatically unique file names under which data and run documentation are stored on disk in the storage device 48. An experimental series of runs is then conducted by cyclic repetition of three phases under the control of the microcomputer 46.

First, the individual run is documented at step 86. The program stored in the control microcomputer 46 then stores a parameter file on disk in the storage device 48. The parameter file contains a record of the experimental conditions pertaining to the previous run. The user then documents the current run by changing the appropriate entries. Prompted parameters entered by the user include column dimensions, identification of stationary and mobile phases, flow rate, temperature as provided by the temperature probes 28 and 30, monitor AUFS, sample size, and identity and concentration of solutes. The user then sets a length of the run and can scale the chromatogram display on a monitor by setting a magnification factor and a zero offset.

The next stage in the data collection program involves the test run itself as indicated in block 88 of FIG. 4. After the sample is manually loaded into the sample loop, the user initiates the test run with an entry on the microcomputer's keyboard 46b in response to a program prompt. The control microcomputer 46 uses the interface circuit 44 to send two digital output signals to the valve controller interface circuit 38 for setting the direction and starting the rotation of the multi-position valve 20. Optical diodes (not shown) within the housing of the multi-position valve 20 encode the instantaneous position of the solvent flow path. This signal is repeatedly monitored by the control microcomputer 46. When the code condition indicating the inject position of the multi-position valve 20 is recognized, the microcomputer 46 sends a signal to stop the rotation of the valve. The program in the control microcomputer 46 then rechecks the orientation code of the valve 20 and if the inject position has been overshot, the directional rotation of the valve is reversed and the valve is moved back to the intended position.

Injection of the sample defines time zero for the run. The run is arbitrarily divided into 1000 data collection intervals. The amplified analog output of the aforementioned optical diode monitor arrangement in the multi-position valve 20 is provided to the A/D converter (not shown) in the interface circuit 44. The average of 10 A/D samplings at the beginning of each data interval constitutes a single data point. After calculating the average data point, the control microcomputer 46 monitors the clock 44a in the interface circuit 44 to permit the procedure to be repeated at the next time point that has been calculated as being the initial time of a data collection interval as carried out in the run block 88 in FIG. 4.

Upon completion of the data collection loop, a data output or storage routine is executed in block 90. The operator is given an opportunity to add a post-run comment, which, for example, may be used to correct a previous documentation entry or to provide an observation relative to later interpretation of the chromatogram. The data are then written onto a magnetic disk within the storage device 48. Two files are generated for each run: one file consisting of the run documentation and the other comprising the 1000 data points collected during the run. Two hard copies of the run are provided by the printer 54: a one page copy of the chromatogram with documentation and an enlarged full page copy of the chromatogram suitable for detailed examination. Because the printer interface card in the printer 54 is "buffered" by its own memory capability and can accept data from the control microcomputer 46 faster than the printer can process it, a second run can be set up and initiated before the printout on the previous run has been completed. A branching operation may be executed at step 92 to either return to the documentation block 86 and repeat the run or terminate the operation at step 94.

If two solute molecules do not interact, then (in dilute solution to ensure chemical ideality) independent elution of the two species will result in a chromatographic profile of a mixture that is equivalent to the arithmetic sum of the absorbance profiles of the two solutes when chromatographed individually. Thus, the difference profile (delta) comparing the experimentally observed elution profile of the mixture with the synthetic summation profile provides a measure of the interaction between two proteins. The delta can be considered an interaction index but is not directly related to the thermodynamic $K_a$ governing the interaction of the solutes because the observed chromatogram of the mixture also depends on the partitioning properties and on the length of the column, sample size, flow rate, and other parameters that determine the ability of the column to separate the solutes while they are dissociated. Nevertheless, within a given set of experimental column conditions, the delta provides useful qualitative, comparative, and, by simulation of the chromatographic process, quantitative information.

Figure 5A:
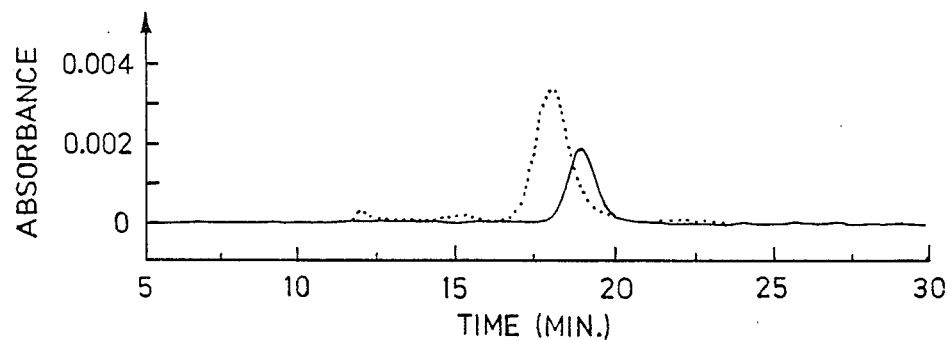
FIGS. 5a, 5b and 5c illustrate the interaction between polyclonal antisera and antigen as measured and displayed by the size-exclusion chromatography system of the present invention.
Figure 5B:
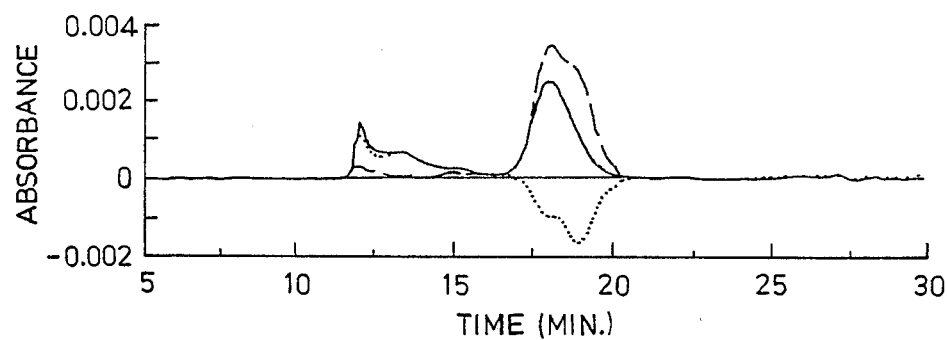
Figure 5C:
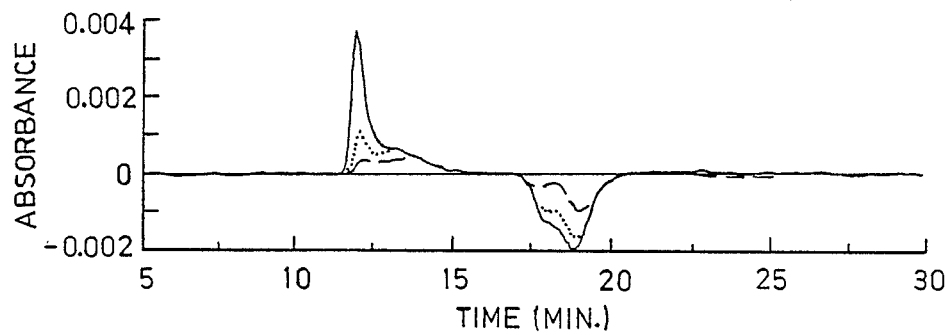

The capability of the size-exclusion chromatography system 10 of the present invention to quickly reveal the presence of an interaction is shown in FIGS. 5a, 5b and 5c. In an experiment the results of which are illustrated in the aforementioned figures, 20 μL mixtures of an Fc fragment obtained from a human IgG myeloma protein and an antiserum specific for human Fc were chromatographed on a TSK-3000 column having dimensions 60 cm×7.5 mm. The run time was 30 minutes.

FIG. 5a shows the elution profiles of the Fc and antiserum components chromatographed separately, where human Fc is illustrated by the solid line plot and the antiserum components are illustrated by the broken line plot. In FIG. 5b, the broken line represents the arithmetic sum of the two profiles observed in FIG. 5a and therefore represents the profile expected if no interaction between the two components is present. The elution profile represented by the solid line, however, was observed when the mixture of Fc and anti-Fc was run. Higher molecular weight species were clearly formed by the interactions of these antigen-antibody interrelated solutes. The dotted line in FIG. 5b represents the delta function and indicates the translocation of protein from lower to higher molecular weight positions. It should be noted that the lower molecular weight negative lobe of the delta function appears to be essentially a "mirror image" of the Fc profile illustrated in FIG. 5a, indicating that nearly all of the Fc participated in the formation of complex, whereas excess, nonparticipating components were present in the antibody zone.

The continuum of proteins eluted between the void volume and the IgG position reflects the formation and dissociation of complexes during the run, as well as the hetergeneity of complex compositions that may be formed by polyvalent antigens and antisera. It is in the nature of large protein antigens to exhibit several different surface targets (epitopes) to which individual antibodies of different specificity can separately bind. A polyvalent conventional antiserum, as opposed to a solution of monoclonal antibody, is composed of a hetrogeneous population of antibodies capable of binding to different epitopes, although in principle each individual antibody binds to a specific epitope. Because each IgG is able to bind two identical epitopes, a single antibody can form a bridge between two antigens. If another antibody binds to a different epitope on one of the antigen-IgG-antigen oligomers, a large lattice of antigen and antibody can be formed. The ultimate size of the lattices is determined by the concentrations, affinities, and ratios of the participants. This is illustrated in the curves of FIG. 5c wherein the protein peak at the excluded volume position (approximately 12 minutes) consists of complexes of apparent molecular weight of 500,000 Da and greater. In general, the largest complexes are expected for a molar equivalence of antibody binding sites and epitopes. Given either an excessive antigen or antibody, lattice formation is incomplete and the transition from antigen excess to near equivalence can be observed from the three profiles plotted in FIG. 5c. The response indicated by the negative lobe of the delta function at the position corresponding to IgG was less for the increase in antibody concentration from 20 (vendor) units/mL to 40 units/mL than for an increase from 10 units/mL to 20 units/mL, suggesting approaching saturation of the available antigen.

There has thus been shown an HPLC-based, small zone, size-exclusion chromatography system for analyzing macromolecular interactions. The size-exclusion chromatography system includes a microcomputer for controlling sample injection and data collection, an HPLC pump, and a commercially available cross-linked agarose resin packed in columns as small as 1 mL volume. The use of a cross-linked agarose resin minimizes the interactions between the solute and matrix. A difference profile (delta) compares the experimentally observed elution profile of the mixture with a simulated summation profile and provides a measure of the interaction between two macromolecules such as proteins. The synthetic summation profile makes use of an algorithm which includes 5 steps in each iterative cycle thereof. These steps include, in sequence, an equilibration calculation (step 1) to determine the free and complexed composition of each cell which is followed by a translation step (step 2). The translation step emulates the migration of the protein through the column on the basis of the velocities of the components and their respective dispersion characteristics. Translation is followed by another cell equilibration (step 3) prior to the execution of a diffusion step (step 4). Diffusion, in addition to dispersion, accounts for band spreading. As the influence of diffusion depends on the concentration gradient, this effect is most prominent early in the run. Step 5 monitors and records the concentration (absorbance) at the detector position. Reequilibration of the cell contents reinitiates the cycle.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

The embodiments of the invention in which an exclusive property or privilege is claimed are defined as follows:

1. Apparatus for determining the extent of interaction between a first macromolecular solute and a second macromolecular solute, said apparatus comprising:
   a chromatographic column;
   first means for introducing the first and second macromolecular solutes into said chromatographic column;
   second means for measuring the concentrations in said chromatographic column of the first and second macromolecular solutes as well as the concentration of a complex formed by said first and second macromolecular solutes and generating an experimental delta function representing the difference between the concentration of said complex and the sum of the concentrations of said first and second macromolecular solutes;
   third means for generating a plurality of simulated delta functions corresponding to a range of association coefficients representing a range of degrees of interaction under various conditions between the first and second macromolecular solutes in forming said complex; and
   fourth means coupled to said second and third means for comparing said experimental delta function with said plurality of simulated delta functions in correlating the measured concentrations of the first and second macromolecular solutes with said range of association coefficients for determining the extent of interaction between the first and second macromolecular solutes.

2. The apparatus of claim 1 wherein said second means includes monitor means for detecting the concentrations of the first and second macromolecular solutes in said chromatographic column.

3. The apparatus of claim 2 wherein said monitor means transmits radiation through the first and second solute of said chromatographic column and responds to the radiation passing through the first and second solutes in detecting their respective concentrations.

4. The apparatus of claim 2 wherein said second means further includes control means coupled to said first means for regulating the amount of the first and second solutes introduced into said chromatographic column.

5. The apparatus of claim 4 wherein said control means includes a microcomputer.

6. The apparatus of claim 5 wherein said first means includes a multi-position valve coupled to and controlled by said microcomputer.

7. The apparatus of claim 6 wherein said first means further includes a manually operated microvalve coupled to said multi-position valve for precisely controlling small amounts of the first and second solutes introduced into said chromatographic column.

8. The apparatus of claim 4 wherein said control means includes input means responsive to user initiated inputs whereby control over said apparatus may be exercised by a user.

9. The apparatus of claim 1 further comprising storage means coupled to said second means for storing data representing the concentrations in said chromatographic column of the first and second solutes.

10. The apparatus of claim 1 further comprising a printer coupled to said second means for providing a graphic presentation of the measured concentrations of and the extent of interaction between the first and second solutes.

11. The apparatus of claim 1 wherein said chromatographic column includes a cross-linked agarose resin matrix through which the first and second solutes are directed.

12. The apparatus of claim 1 wherein said third means includes a simulation computer.

13. A method for measuring the interaction between first and second macromolecular solutes in forming a complex, said method comprising:
   depositing the first and second solutes in a chromatographic column at a first location therein;
   measuring the concentrations of unreacted portions of the first and second solutes as well as the concentration of a complex formed by the first and second solutes at a second location in said chromatographic column;
   taking the difference between the concentration of the complex and the sum of the concentrations of the first and second solutes in generating an experimental delta function;
   generating a plurality of simulated delta functions corresponding to a range of association coefficients representing a range of degrees of interaction between the first and second solutes under various conditions;

comparing the experimental delta function with the plurality of simulated delta functions; and correlating the measured concentrations of the first and second solutes with said range of association coefficients in providing a quantitative measure of the interaction between the first and second solutes.

14. The method of claim 13 wherein the step of generating a range of association constants includes simulating movement of the first and second solutes for various velocity, diffusion and dispersion values thereof.

15. The method of claim 14 wherein the step of generating a range of association constants further includes the sequential steps of dividing said chromatographic column into a plurality of cells, determining the composition of each cell in terms of the first and second solutes and the complex, advancing the first and second solutes through said chromatographic column from cell to cell, and again determining the composition of each cell until the first and second solutes exit the chromatographic column.

16. The method of claim 14 wherein the step of comparing the concentrations of unreacted portions of the first and second solutes with the range of association constants includes comparing simulated and experimental elution profiles obtained at different initial concentrations of the first and second solutes.

* * * * *